United States Patent [19]

Shelton et al.

[11] Patent Number: 5,079,843
[45] Date of Patent: Jan. 14, 1992

[54] HOLE CUTTER FOR OSTOMY ADHESIVE WAFERS

[76] Inventors: Joseph A. Shelton, 626 S. Columbus Blvd., Tucson, Ariz. 85711; Jay G. Shelton, 3114 Newell St., Riverside, Calif. 92507; Jack A. Shelton, 511 Wellesley Dr., Apt. 104, Corona, Calif. 91714

[21] Appl. No.: 633,791

[22] Filed: Dec. 26, 1990

Related U.S. Application Data

[63] Continuation-in-part of Ser. No. 580,157, Sep. 10, 1990, abandoned.

[51] Int. Cl.$^5$ .......................... B26B 5/00; B26B 3/00
[52] U.S. Cl. ........................................ 30/310; 30/300
[58] Field of Search ................. 30/300, 310, 316, 320, 30/299

[56] References Cited

U.S. PATENT DOCUMENTS

| | | | |
|---|---|---|---|
| 422,666 | 3/1890 | Tull . | |
| 787,348 | 4/1905 | Hansen . | |
| 1,924,717 | 8/1933 | Hall | 30/300 |
| 2,612,686 | 10/1952 | Wagner . | |
| 3,456,346 | 7/1969 | Snyder | 30/310 |
| 3,948,256 | 4/1976 | Schneider . | |
| 4,010,543 | 3/1977 | Nusbaum . | |
| 4,060,893 | 12/1977 | Matsuura | 30/310 |
| 4,102,045 | 7/1978 | Bergh . | |
| 4,252,120 | 2/1981 | Carpenter . | |
| 4,277,891 | 7/1981 | Dick . | |
| 4,391,042 | 7/1983 | Sunderland . | |
| 4,548,118 | 10/1985 | Brosch | 30/310 |
| 4,593,467 | 6/1986 | Safar | 30/310 |
| 4,681,574 | 7/1987 | Eastman . | |
| 4,782,730 | 11/1988 | Picone et al. | 30/300 |
| 4,817,287 | 4/1989 | Arnold . | |
| 4,911,051 | 3/1990 | Depetris | 30/310 |

*Primary Examiner*—Douglas D. Watts
*Assistant Examiner*—Paul M. Heyrana, Sr.
*Attorney, Agent, or Firm*—J. Michael McClanahan

[57] ABSTRACT

An adjustable size hole cutter for ostomy adhesive wafers is disclosed having firstly a cylindrical body adapted to hold a cutting blade, a cylindrical pilot protruding outward from the bottom circular face of the cylindrical body to reside in a preformed hole in the colostomy wafer, and a Tee handle protruding outward from the top face. Adjustment of the blade's distance from the center of the cylindrical body for cutting different sized holes is accomplished by means of removable adjustment spacers situated in a radial slot formed in the wall of the cylindrical body, the cutting blade secured to the outside adjustment spacer by a set screw passing through a hole in the blade and aligned holes in the adjustment spacers. A circular base plate with centrally located hole receives the pilot of the adjustable hole cutter. The ostomy wafer is placed between the bottom face of the cylindrical body and the base plate whereupon the blade cuts into the wafer and the circular hole cut as the cutter is rotated. In alternate embodiments, slots are selectively situated in the bottom circular face of the cylindrical body to receive a blade at the diameter of choice. In addition, a cylindrical cutter provides for initially making the pilot hole in ostomy wafers not furnished with one.

15 Claims, 1 Drawing Sheet

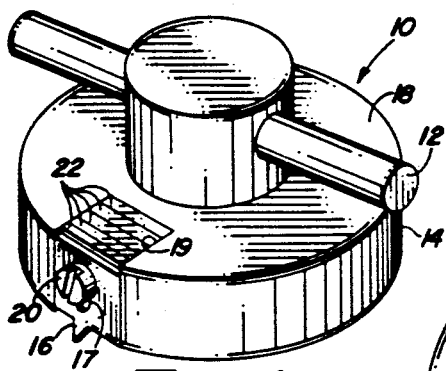
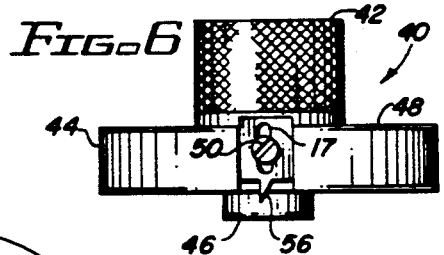
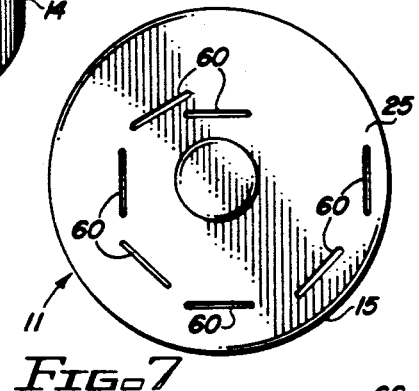
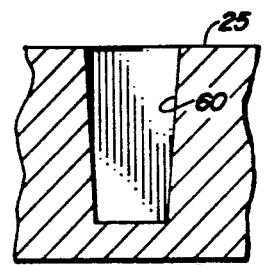
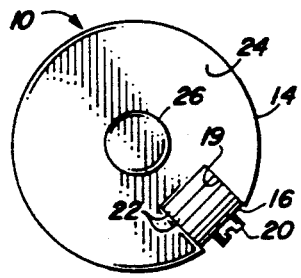
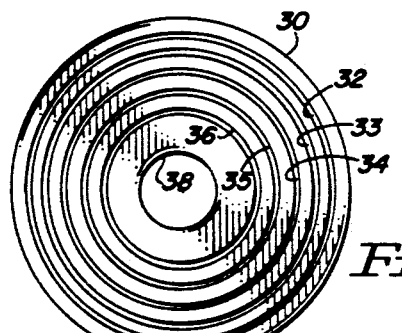
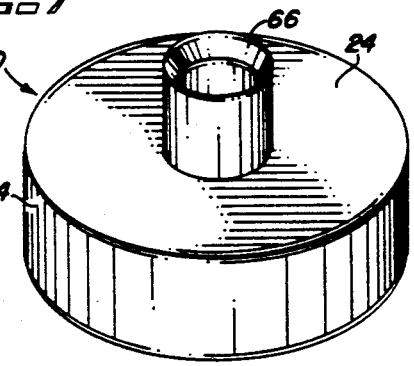
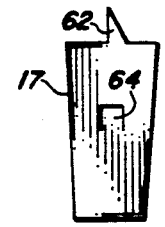
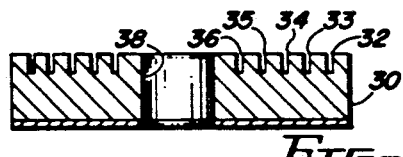
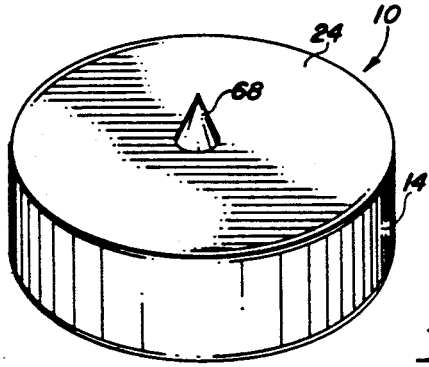
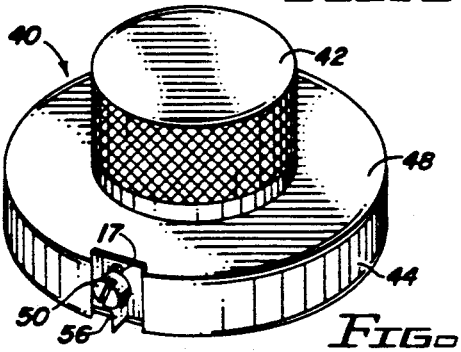
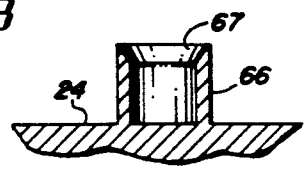
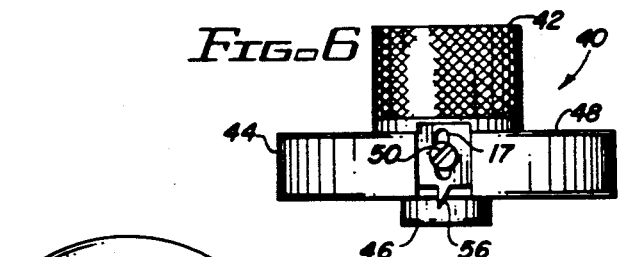

HOLE CUTTER FOR OSTOMY ADHESIVE WAFERS

This is a continuation-in-part of copending application Ser. No. 580,157 filed on Sept. 10, 1990, abandoned 12/26/90.

BACKGROUND OF THE INVENTION

1. Field of the Invention

The field of the invention is devices adapted to enlarge holes in the ostomy adhesive wafers for use by colostomy, ileostomy, and urostomy patients.

2. Description of the Related Art

In patients who have had extensive medical problems with their colon, ileum, bladder, or kidneys, it is sometimes necessary that the colon, ileum, or tubes from the bladder or kidneys be routed from their normal attachments to an opening on the body in the lower abdomen region, many times in about the area immediately below where a person wears their belt. A stoma is an opening made in the skin covering the abdomen to which the lower end of the colon, ileum, or other tube has been attached. Many times the patient is given no means by which to control the flow of wastes through the upper or lower bowels or bladder and out the opening or stoma made in the stomach or abdomen wall. As a consequence, measures must be made to receive and hold these waste products. To accomplish this, various medical supply companies distribute apparatus for the collection of urine and feces. This apparatus generally consists of an ostomy bag which is supported upon the body of the patient, the bag having an upper opening which encompasses the stoma opening.

The problem with the ostomy apparatus is that an air and water tight seal must be made between the upper opening of the ostomy bag and the stoma in the wall of the abdomen in order to maintain sanitary conditions. To this end, the medical supply companies provide an adhesive wafer which adheres to a person's skin, the wafer being flat and annular in shape and adapted to encompass the periphery of the opening in the abdomen wall. On one side of the wafer is a non-skin irritating adhesive for holding the wafer to the person's skin and on the other flat side of the wafer is attached an annular plastic ring, the ring so configured to be encompassed by a second ring which forms the opening of the ostomy bag in a waterproof seal.

Most ostomy wafers are provided with a nominal ⅛ inch diameter central pilot opening which, in the majority of the patients cases, must be enlarged to accommodate the size of the particular patient's stoma since it is not desirable or sanitary to block or partially block the flow of the wastes from the patient's body into the ostomy bag.

Accordingly, the ostomy bag kits provided by the medical supply companies provide instructions to the patient to enlarge the opening through the ostomy wafer utilizing a pair of scissors, all of this accomplished before the ostomy wafer is placed on the skin of the person. To aid in enlarging the opening through the wafer, and to protect against contamination, a detachable plastic or paper cover is adhered to the adhesive on the wafer. This cover is then removed prior to the attachment of the wafer to the patient.

Various devices have been devised to enlarge this ostomy wafer opening and have been disclosed in various patents as follows. These devices take the form of a punch utilizing a circular cutting edge which is forced through the ostomy wafer. The first, being a pliers type punch, is seen in the 1989 patent to Arnold, U.S. Pat. No. 4,817,287 where, in the jaws attached to the handle of the pliers open and close, one of the jaws has the attached annular cutting blade and the other has a disk with an annularly shaped cutting groove therein. The ostomy wafer is placed between the jaws of the pliers with the central opening of the wafer generally centrally located in the disc having the cutting groove. The handles of the pliers are brought together to force the jaws together to cut the opening through the wafer.

The other type of punch type ostomy wafer known to the inventor is shown in a 1983 patent to Sunderland, U.S. Pat. No. 4,391,042, wherein a non-circular opening is made by using a similarly shaped cutting element. The device is positioned over the already existing hole in the adhesive wafer and with a handle attached to the cutting element, the cutting edge is forced through the wafer. The wafer rests upon a support block of wood during the punching operation, the wood having a cover of vinyl plastic.

While the above devices obviously do accomplish their purpose of enlarging the opening through the ostomy wafer, yet they do require some amount of force on the part of the patient or other operator to push the cutting edge through the ostomy wafer. Inasmuch as many ostomy patients may be elderly, the required application of force to a pliers type instrument or to a punch type instrument may be more than the patient is capable of.

In addition, it is obvious from using the punch type ostomy wafer hole cutters of the above two patents, means are needed to reasonably assure that the newly cut opening through the wafer is generally centrally located. If the opening to be enlarged was not directed to be centrally located, opportunity for the patient to place the opening too close to the outer peripheral edge of the wafer is provided. In such event, opportunity for leakage of the contents of the bowel to pass by the adhesive may be possible if there is insufficient width of the adhesive around the ostomy wafer opening for a full sealing.

Accordingly, it is readily apparent that there is need for apparatus which will enlarge the already existing opening through the ostomy wafer with a new opening which is concentric with the previously formed opening in order to ensure that as much adhesive as possible is present on all parts of the adhesive wafer surrounding the opening.

It is also obvious that there is need for an ostomy wafer hole cutter which may be operated by a person without the application of force needed to punch a hole through the ostomy wafer.

SUMMARY OF THE INVENTION

The embodiment of the invention described consists of a hole cutter for ostomy adhesive wafers which is easy to handle and easy to operate consisting of a guided single blade which, when rotated about the opening provided in the ostomy wafer, circumscribes a new enlarged opening.

In construction, the invention consists of a cylindrical body having operable mounted at its periphery a protruding blade adapted to cut the ostomy wafer as the cylinder is rotated. To accomplish rotation of the cylinder, a Tee handle is provided attached to the top of the cylindrical body and in axial alignment. Lastly, to assure that the blade at or near the periphery of the cylindrical body inscribes a circle concentric around the already provided opening in the ostomy wafer, a cylindrical pilot adapted to rotatably reside in the provided hole is attached to the bottom flat circular surface of the cylindrical body opposite the top surface having the knurled handle. In an alternate embodiment, a cylindrical knurled handle is substituted for the Tee handle. All cylindrical portions of the invention, i.e., the knurled or Tee handle on top, the cylindrical body holding the blade, and the pilot are all in axial alignment.

The inventive hole cutter is used in combination with a base plate, the base plate being a circular disk shaped plate having at its center an opening to receive the pilot. Surrounding the center opening is a plurality of concentric grooves cut in the top flat circular surface of the base plate adapted to receive the cutting blade as the blade cuts through the ostomy wafer. It is not intended that the blade should cut a path in the base plate as it is being used.

The ostomy wafer whose preformed pilot hole is to be enlarged is placed first upon the flat circular bottom side of the hole cutter with the hole cutter's pilot protruding through the preformed opening. The hole cutter, together with the ostomy wafer, is then placed upon the base plate with the pilot of the hole cutter entering the central opening of the base plate. The invention may be held in the hands of the operator, one hand holding the base plate and the other hand holding the knurled or Tee handle to rotate the blade through the ostomy wafer. Alternatively, the base plate may be placed upon the top of a desk or other flat surface and then the knurled or Tee handle rotated by the operator to circumscribe the new opening. Since the pilot of the hole cutter does not protrude out through the base plate, a nonskid surface may be placed upon the bottom of the base plate whereupon by placing the base plate upon a flat surface, it need not be held when the knurled or Tee handle is rotated.

In the preferred embodiment, means are provided to cut openings of various diameters. This is accomplished by varying the distance of the cutting blade from the axial center of the cylindrical body with spacers. Firstly, a radial slot is formed in the cylindrical body from the outer cylindrical peripheral surface radially inward. Into this rectangular slot may be placed one or more rectangular spacers. Each spacer is characterized by having a hole through its center. The blade is an elongated flat plate having at one end a cutting point and a centrally located slot. Through this slot passes the threaded shaft of a set screw which secures the blade to the cylindrical body, the threaded shaft of the set screw passing through the blade slot and the openings through each of the spacers into a threaded blind hole radially set in the cylindrical body and through its axial center. The number of spacers utilized determines the distance of the blade from the axial center and thus the diameter of the cut circle.

The depth of the blade may be varied as needed by first loosening the set screw, adjusting the blade depth by moving it up or down (the shaft of the set screw riding in the blade slot), and then tightening the set screw when the depth desired is set.

In an alternate embodiment of the invention, no provision is made to variably adjust the diameter of the opening to be cut in the ostomy wafer and the blade is mounted at the periphery of the cylindrical body. In most cases, the diameter of the cylindrical body is reduced in diameter from the cylindrical body of the preferred embodiment. A very shallow slot is longitudinally cut in the outside peripheral surface of the cylindrical body of the alternate embodiment such that the sides of the blades engage the sides of the slot, as they do in the preferred embodiment, to hold the blade against rotation about the set screw. The set screw again has its shaft residing in the slot of the blade and once the depth of the blade point has been adjusted, the set screw is tightened.

Still other alternate embodiments of the invention provide means to set the blade into one of a plurality of preformed slots variously spaced at stategic points on the bottom circular face of the cylindrical body. To accommodate one or more of the slots, the blade is equipped with a specially formed angularly protruding outward tang such that once the blade is inserted into the appropriate slot, the blade will remain there.

In still other alternate embodiments, means are attached to the cylindrical body for those few cases where no preformed pilot hole is provided in the ostomy wafer. In these cases, the subject invention is modified to create its own pilot hole by providing, in the place of the usually protruding outward pilot, a centrally located cylindrical cutter and/or punch which cuts or punches a pilot hole in the ostomy wafer material prior to penetration of the cutting blade for rotatably cutting the desired sized hole. Here, if the ostomy wafer is not provided with a pilot hole, the invention first provides that pilot hole and operates around the newly formed pilot hole as does the preferred embodiment.

In a final embodiment of the invention, and also for those few cases where the ostomy wafer provides no preformed pilot hole, a cone-shaped sharpened point centrally located in the flat bottom circular face of the cylindrical body provides means by which the cylindrical body is secured to the ostomy wafer just immediately prior to circumscribing the hole desired to be cut out.

It is an object of the subject invention to provide a hole cutter for ostomy adhesive wafers which may be manipulated and utilized without the application of much force.

It is another object of the subject invention to provide a hole cutter for ostomy adhesive wafers wherein an enlarged opening may be formed in the wafer which is concentric to the existing pilot opening of the wafer.

It is still a further object of the subject invention to provide a hole cutter for ostomy adhesive wafers wherein holes of various diameters may be formed.

Other objects of the invention will in part be obvious and will in part appear hereinafter. The invention accordingly comprises the apparatus possessing the construction, combination of elements, and arrangement of parts which are exemplified in the following detailed disclosure and the scope of the application invention which will be indicated in the claims.

BRIEF DESCRIPTION OF THE DRAWINGS

For further understanding of the features and objects of the subject invention, reference should be had to the following detailed description taken in connection with the accompanying drawings wherein:

FIG. 1 is a perspective view of the subject inventive adjustable diameter hole cutter for ostomy adhesive wafers;

FIG. 2 is a bottom view of the subject invention;

FIG. 3 is a top view of the circular disk base plate used in combination with the adjustable diameter hole cutter;

FIG. 4 is a cross-sectional view of the circular disk base plate;

FIG. 5 is a perspective view of an alternate embodiment of the adjustable diameter hole cutter;

FIG. 6 is a side view of the alternate embodiment of the invention shown in FIG. 5;

FIG. 7 is a bottom view of the alternate embodiment of the invention showing the blade receiving slots;

FIG. 8 is a diagram showing the side view configuration of the slots shown in FIG. 7;

FIG. 9 is a side view of the blade which may reside in one of the slots;

FIG. 10 is a partial end view of the blade of FIG. 9 showing the angularly protruding tang;

FIG. 11 is a perspective view of an alternate embodiment of the invention showing the bottom flat circular face with the pilot hole cutter and/or punch;

FIG. 12 is a sectional view taken through the pilot hole cutter and/or punch of FIG. 11; and FIG. 13 is a perspective view of the bottom flat circular face showing a centrally located cone-shape sharpened point serving as pilot.

In various views, like index numbers refer to like elements.

DETAILED DESCRIPTION OF THE PREFERRED EMBODIMENT

Referring now to FIG. 1, a perspective view of the preferred embodiment of the adjustable diameter hole cutter 10 for a ostomy adhesive wafer is shown. The major elements of the adjustable hole cutter 10 comprises Tee handle 12, cylindrical body 14, a cylindrical pilot, and blade 16. Not shown is the pilot which resides centrally to cylindrical body 14 on the opposite side from Tee handle 12. Firstly, cylindrical body 14 is the primary element and consists of a solid cylinder having two oppositely situated flat circular faces with Tee handle 12 protruding outwardly from the top flat circular face 18 of cylindrical body 14. Tee handle 12 has a cylindrical rod passing transversely through an outstanding cylindrical boss attached to top flat circular face 18, the axis of the cylindrical boss aligned with the cylindrical axis of body 14. Tee provides easy holding by the patient or operator without slippage in their fingers. Attached at the periphery surface of cylindrical body 14 is cutting blade 16 which has its cutting point extending below the bottom flat circular surface of cylindrical body 14. The depth of blade 16 is set by tightening set screw 20 which has its threaded shaft passing through slot 17 formed in the blade itself. Adjustment up or down of blade 16 may be accomplished by loosening set screw 20, adjusting the depth of blade 16 to the desired depth, and then tightening set screw 20.

It is noted that a radial slot or channel of a constant width is formed or cut completely through the thickness or solid wall of cylindrical body 14 intersecting both top and bottom flat circular surfaces. The channel or slot may be filled with adjustment spacers 22, of which five is seen in FIG. 1, to provide for various diameter circular holes to be cut by the invention. For convenience, 3 spacers are ⅛ inch thick and 2 are 1/16 inch thick. This allows ⅛ inch differences in hole diameters. The threaded shank of set screw 20 passes through formed holes or openings in adjustment spacers 22 in order that both the blade 16 and the adjustment spacers 22 are secured by set screw 20. In the preferred embodiment, set screw 20 has a slot adapted to receive the blade of a screwdriver.

FIG. 2 is a bottom view of the inventive adjustable hole cutter 10 for ostomy adhesive wafers as shown in FIG. 1. Here, primarily seen is the bottom flat circular face 24 of the invention showing pilot 26 centrally located on circular face 24. Pilot 26 is a cylindrical boss protruding outward from circular face 24. Also shown is the radial slot or channel cut through the thickness or solid wall of cylindrical body 14 to receive the adjustment spacers 22. Blade 16 (seen on end) and adjustment spacers 22 are held in place by set screw 20.

In the embodiment shown in FIG. 2, adjustable hole cutter 10 has been set for cutting the largest circle possible with the invention wherein blade 16 is at the maximum distance from the center of cylindrical body 14 (and also pilot 26), by use of the maximum number of adjustment spacers. It is realized of course that even more adjustment spacers could be added however, it is preferred that the blade 16 should have its sides engaging the sides of slot 19 formed in cylindrical body 14 to prevent the blade from rotating around set screw 20. Therefore, the diameter of cylindrical body 14 is just large enough to receive the maximum number of adjustment spacers and leave just a small amount of slot 19 unfilled. The blade is preferably the same width as slot 19.

Referring now to FIG. 3, a top view of base plate 30 is shown. Base plate 30 is a cylindrical disk having a centrally located pilot hole 38. Pilot hole 38 is adapted to receive pilot 26 of adjustable hole cutter 10 when it is being used. Formed at intervals between pilot hole 38 and the outside peripheral surface of base plate 30 are a plurality of grooves 32 through 36, these grooves just slightly wider and deeper than the thickness and expected depth of blade 16, which should be minimal into base plate 30. The concentric grooves 32 through 36 are set at the various radius which blade 16 would take using the adjustment spacers 22 shown in FIG. 2 or, with the inner groove 36, no adjustment spacer used and blade 16 setting at the very bottom of slot 19 in cylindrical body 14. In the preferred embodiment, the thickness of base plate 30 is at least greater than the length of pilot 26 so that when adjustable hole cutter 10 is placed upon base plate 30, pilot 26 will not bottom out (or completely protrude through).

In the preferred embodiment, the subject adjustable hole cutter was formed of aluminum metal, although it could be made of injected molded plastic. The base plate was made of press-board, although it too could be made of injected molded plastic. The diameter of cylindrical body 14 was 2 inches so that, with all adjustment spacers in place, the largest diameter hole that may be cut from the ostomy adhesive wafer would be 2 inches. In the preferred embodiment, three adjustment spacers were ⅛ inch thick and two were 1/16 inch thick, all being 5/16 inch wide to correspond with the 5/16 inch radial slot or channel 19 formed in cylindrical body 14. Accordingly, by selection of adjustment wafers, the change of diameter of the resultant hole which may be cut is ⅛ inch, the second largest then being 1⅞ inch, and so on to, lastly 1 inch. The diameter of round pilot 26 which protrudes from the bottom flat circular face 24 was ⅛ inch and it protruded ⅛ inch. The thickness of ostomy adhesive wafers is usually less than 1/16 inch.

FIG. 4 shows a cross-sectional view of base plate 30 detailing pilot hole 38 which passes completely through base plate 30 and circular grooves 32 through 36, the grooves only passing a short depth into the top surface of base plate 30.

In the preferred embodiment, Tee handle 12 stood out from top flat circular face 18 a distance of 1 inch and the thickness of cylindrical body 14 was ⅛ inch. The blade was as wide as was slot 19, namely 5/16 inch, had a thickness of about 1/64 inch and total length of 11/16 inch.

Referring now to FIG. 5, an alternate embodiment of the device as shown in a perspective view wherein the adjustability feature of the preferred embodiment has been eliminated, thus eliminating radial slot or channel 19 of hole cutter 10 and choosing for cylindrical body 44 a diameter of 1¼ inch. Blade 56 is set into a recess or longitudinal slot formed in the cylindrical wall of body 44 such that blade 56 cuts out a circle right at the diameter of cylindrical body 44. The recess also secures the blade from rotating. Knurled handle 42 projects outwardly of top flat circular surface 48, knurled handle having a height of 1 inch and a diameter of 1 inch. It has been determined that handles of this size are also easy and comfortable to use. Holding blade 56 in place is set screw 50, set screw 50 having a slot formed in it to receive a flat bladed screw driver for tightening. Naturally, threads are formed into cylindrical body 44 to receive the threads of set screw 50.

FIG. 6 is a side view of the alternate embodiment showing firstly, protruding cylindrical boss pilot 46 adapted to be received in the starting hole in the ostomy wafer and also into the pilot hole 38 of the base plate shown in FIGS. 3 and 4, which is also used with the alternate embodiment. Immediately at the base of pilot 56 is the bottom flat circular surface 54 of cylindrical body 44. Opposite bottom flat circular surface 54 is top flat circular surface 48 with outstanding protruding knurled handle 42. Lastly, blade 56 is seen situated in the recess formed in the peripheral wall of cylindrical body 44, the cutting edge of blade 56 extending below bottom flat circular surface 54 a short distance, but sufficient to cut through a ostomy adhesive wafer, and not as deep as the length of pilot 46. It is noted that all of the cylindrical bodies that make up the alternate embodiment, as in the preferred embodiment, have their cylindrical axis in alignment.

Although in the alternate embodiment above, a diameter of 1¼ inches was chosen at which to place the cutting blade, it is realized that any dimension could be utilized for the diameter of the cylindrical body and thus the diameter of the cut circle. Obviously also, the alternate embodiment shown in FIGS. 5 and 6 may be used with the base plate shown in FIG. 3 which, if accomplished, would have blade 56 of the alternate embodiment 40 riding in circular groove 34. Again, pilot 46 of the alternate embodiment mates with pilot hole 38 of base plate of FIG. 3.

FIG. 7 is a view of bottom flat circular face 25 of alternate embodiment hole cutter 11 wherein radial slot 19 shown in the preferred embodiment of FIGS. 1 and 2 is absent as is the blade usually positioned in radial slot 19 and the adjustment wafers. Rather, alternate hole cutter 11 has a plurality of blind opening slots 60 formed into cylindrical body 15, their openings communicating only to the bottom flat circular face. Each slot is situated in one of eight sections of the circle forming face 25 and the slots arranged in outwardly spiraling fashion around the pilot 27. It is noted that there are only seven slots shown so that one of the eight sections will be unfilled. Since these slots run almost through the thickness of cylindrical body 15, placing them in spiral staggered fashion results in less compromising of the structural strength of cylindrical body 15. This is especially important since it is anticipated that alternate hole cutter 11 will be made of plastic by the injection mold process.

Progressing outward, each of the slots in the alternate embodiment of FIG. 7 is spaced an additional 1/16 inch outward from the center of pilot 27 so that, as will be explained later, when blades are inserted into one or more of these slots, the difference in hole diameters cut is ⅛ inch. With the embodiment of FIG. 7, it is possible to selectively cut holes in the ostomy wafer from a minimum ⅞ inch diameter to maximum 2 inch diameter providing, of course, that the inmost slot is ⅞ inch from the center of pilot 27.

Referring now to FIG. 8, a full side view of slot 60 (as if removed from alternate embodiment 11) is shown. This slot is slightly trapezoidal in shape and in the alternate embodiment, suggested dimensions are ⅝ (0.625) inches high (or long) and 5/16 (0.3125) inches wide at the top. The bottom would be nominally 0.3000 inches, narrowing by taper of 0.00625 inches on each side. The thickness of the slot will be nominally 25/1000 inch throughout its total length or height, the thickness not varying. It is realized of course, that adjustments in the dimensions may well be necessary to accommodate the injection molding process. In fact, measures to accommodate possible loose fitting blades may be seen in the next figure wherein a full side view of a proposed blade 17 is shown. It is also noted that the thickness of cylindrical body 14 shown in the preferred embodiment of FIG. 1 was suggested to have a thickness of ⅛ inch. It is suggested here, when building the alternate embodiment, that this thickness be increased to ¾ inch since it is intended that slot 16 be a blind opening.

In FIG. 9, blade 17 shown in full side view is designed to have the same dimensions (length, width, thickness) as slot 60 (not including the cutting point 62). Blade 17 was made of thin sheet steel in the embodiments. It is apparent that blade 17 may be pushed down into slot 60 of hole cutter 11 and frictionally held there, all portions of blade 17 being within the body of cylindrical body 15 except for the cutting point 62. It is obvious that in pushing blade 17 into one of the slots 60 shown in hole cutter 11, those portions of blade 17 on opposite sides of cutting point 62 must be used. One suggested tool that might be used is the spool from a spool of thread since it has a central hole which could receive cutting point 62 during time of pushing. Of course, measures must be taken to assure that the sides of the spool do not interfere with pilot 27.

To assure that blade 17 does not come out of its slot in hole cutter 11, tang 64 is formed in the blade material, the tang formed by punching the inverted "U" shaped tang 64 shown in FIG. 9. This angularly outwardly protruding tang, while not greatly impeding pushing of blade 17 into slot 60, does greatly impede removal of the blade.

A partial side view of blade 17 is shown in FIG. 10 at around the area of tang 64. Here is seen tang 64 formed in blade 17 pushed slightly outward at an angle such that the square punched edge of the tang protrudes a small distance from the side of blade 17. By this means, as blade 17 is pushed into slot 60, tang 64 will not interfere with the insertion of the blade, tang 64 just being pushed back slightly from its most outward position. However, if one attempted to pull blade 17 out, the right angle edge of tang 64 will dig into the side of slot 60. Thus, for all practical purposes, blade 17 is fixedly secured into its position in slot 60 in the ostomy wafer hole cutter 11.

It is realized of course that the alternate embodiment shown in FIGS. 7-10 still are embodiments of the preferred embodiment 10 (FIGS. 1 and 2) and that the only change has been in the securing of the cutting blade. The alternate embodiment 11 will still have the same thick cylindrical body and Tee handle as shown in the preferred embodiment. It may also incorporate the knurled handle shown in FIG. 5.

Still other embodiments of the invention are possible, such as those shown in FIGS. 11-13. The inventor has determined that a small percentage of ostomy wafers available to the public are wafers without a pilot hole. These ostomy wafers, even through they have no pilot hole, still must have a hole cut through them by which to pass waste into the ostomy bag. Therefore, the preferred embodiment of FIG. 1 has been modified to substitute for pilot 26 a new pilot 66, the new pilot being a circularly cutting cylindrical shell which may rotatably cut a pilot hole or punch a pilot hole. This new pilot is located upon the bottom flat circular face 24 of cylindrical body 14 of hole cutter 10. The slot 19 and adjustment spacers, together with the blade are not shown in this perspective view of FIG. 11 for purposes of ease of illustration. In FIG. 11, circularly cutting cylindrical shell which becomes pilot 66, being hollow, collects the round disks or tabs of ostomy wafer within its interior. After a while, it is realized that these round disks would have to be dug out with a pocket knife or ice pick. Of course it is entirely possible to drill a hole through cylindrical body 14 and through knurled handle 12 (not shown) from which the round tabs of cut pilot holes of ostomy wafer may be pushed completely through the device. In fact, if that hole, at least through a knurled handle and a portion of the cylindrical body, were larger than the inside diameter of circular cutting cylindrical shell pilot 66, these round tabs will fall out on their own accord after the interior to pilot 66 is filled up.

In using the invention of FIG. 11, the approximate center of the ostomy wafer is located. The party then pushes pilot 66 through the colostomy wafer at that point or rotates the Tee or knurled handle to rotatably cut the pilot hole. Once the pilot hole has been cut and pilot 66 is resting in it, the cutting blade may proceed to cut out the desired opening in the ostomy wafer by rotation of the handle.

FIG. 12 is a cross-sectional view taken through pilot 66 showing cutting edge 67 at the top end, cutting edge 67 situated around the inside of the thickness of the cylindrical shell comprising pilot 66. It is realized of course that the chamfer of cutting edge 67 could start on the opposite side of the thickness of the cylindrical shell from that shown and there way may well be advantages to that.

Lastly, referring to FIG. 13, still another embodiment of the preferred embodiment of hole cutter 10 shown in FIG. 1 is detailed in a perspective view of the bottom flat circular face 24 and cylindrical body 14. Here, pilot 26 is replaced by a cone-shaped sharpened point 68 which, like the embodiment of FIG. 11, is for use with ostomy wafers where no preformed pilot hole is provided. In this case, once the approximate center of the ostomy wafer is determined, point 68 is then inserted into the ostomy wafer and then hole cutter 10 rotated wherein the blade, as shown in FIG. 1, proceeds to cut out the desired opening through the ostomy wafer for use by the patient. Thus it is apparent that cone-shaped point 68 is another method of securing hole cutter 10 to the ostomy wafer for the cutting operation where no pilot hole is provided for pilot 26 of the preferred embodiment.

While a preferred embodiment of the invention, together with an alternate embodiment, has been shown and described, it is appreciated that other such embodiments of the invention are possible and that there is no intent to limit the invention by such disclosure, but rather it is intended to cover all modifications and alternate embodiments falling within the spirit and the scope of the invention as defined in the appended claims.

We claim:

1. A hole cutter for ostomy adhesive wafers comprising:
    a cylindrical body having an axial center, said cylindrical body having a cylindrical axis, a top and bottom flat circular face, an exterior cylindrical peripheral surface, a radial slot formed in said cylindrical body intersecting said top and bottom flat circular face in said exterior cylindrical peripheral surface, said slot having parallel sides, and a pilot attached to said bottom flat circular face, said pilot defining a protruding cylindrical boss, said pilot having a cylindrical axis in alignment with said cylindrical body axis;
    a cutting blade attached to said cylindrical body residing in said radial slot of said cylindrical body, said cutting blade for cutting holes in the ostomy adhesive wafers; and
    a handle attached to said cylindrical body whereby a person may grasp the handle and, by rotating said handle, cause said cylindrical body to rotate along with said cutting blade and thereby cut a circle in the ostomy adhesive wafer.

2. The hole cutter for ostomy adhesive wafers as defined in claim 1 further including a plurality of adjustment spacers, said adjustment spacers adapted to removably reside in said radial slot, said adjustment spacers operably engaging said cutting blade whereby the distance of the cutting blade from said cylindrical body axis may be adjusted by said adjustment spacers.

3. The hole cutter for ostomy adhesive wafers as defined in claim 2 further including a base plate, said base plate having an opening therein adapted to receive said cylindrical boss pilot whereby the ostomy adhesive wafer may be placed upon said base plate and said pilot passed through an opening in the ostomy adhesive wafer into said opening in said base plate, said handle thereby cutting through the adhesive wafer to form the hole when rotated.

4. The hole cutter for ostomy adhesive wafers as defined in claim 3 wherein said base plate includes a plurality of concentric grooves surrounding said opening in said base plate, said concentric grooves adapted to receive said cutting blade when said cylindrical body resides on said base plate with said cylindrical boss pilot situated in said opening of said base plate, said base plate concentric grooves allowing said cutting blade to rotate without engaging said base plate.

5. The hole cutter for ostomy adhesive wafers as defined in claim 4 further including a set screw, said set screw engaging said cutting blade, adjustment spacers, and cylindrical body.

6. The hole cutter for ostomy adhesive wafers as defined in claim 5 wherein said cutting blade includes an elongated slot and each of said plurality of adjustment spacers includes an opening, said cutting blade elongated slot and said opening of said adjustment spacers adapted to receive said set screw whereby said cutting blade may be held in place by said set screw for various sized hole cuttings.

7. The hole cutter for ostomy adhesive wafers as defined in claim 6 wherein said handle defines a Tee handle operably attached to said cylindrical body top circular surface, said Tee handle having a cylindrical boss attached to said cylindrical body top circular surface and an elongated rod passing transversely through said cylindrical boss, said cylindrical boss having an axis in alignment with the axis of said cylindrical body.

8. The hole cutter for ostomy adhesive wafers as defined in claim 7 wherein said base plate defines a top surface and a bottom surface, said top surface receiving said concentric grooves, and a non-skid surface adhered to said base plate bottom surface.

9. The hole cutter for ostomy adhesive wafers as defined in claim 6 wherein said handle defines a cylindrical knurled handle attached to said cylindrical body top circular surface, said cylindrical knurled handle having a cylindrical axis in alignment with the axis of said cylindrical body.

10. The hole cutter for ostomy adhesive wafers as defined in claim 1 wherein said pilot comprises an outwardly protruding cylindrical shell having a sharpened chamfered edge, said sharpened chamfered edge adapted to cut a pilot opening in the ostomy adhesive wafer and then reside in the pilot opening as said hole cutter is rotated.

11. The hole cutter for ostomy adhesive wafers as defined in claim 1 wherein said pilot defines an outwardly protruding cylindrical cone, said cylindrical cone having a point adapted to penetrate into the ostomy adhesive wafer to secure said hole cutter as said hole cutter is rotated.

12. A hole cutter for ostomy adhesive wafers comprising:

a cylindrical body having a cylindrical axis, a top and bottom flat circular face, an exterior cylindrical peripheral surface, a pilot operably attached to said bottom flat circular face, said pilot having a cylindrical axis in alignment with said cylindrical body axis, and a plurality of slots formed in said cylindrical body, each of said plurality of slots having an opening communicating with said cylindrical body bottom flat circular face;

a cutting blade adapted to be received in each of said plurality of slots, said cutting blade for cutting holes in the ostomy adhesive wafers;

a handle attached to said cylindrical body whereby a person may grasp the handle and, by rotating said handle, cause said cylindrical body to rotate along with said cutting blade and thereby cut a circle in the ostomy adhesive wafer.

13. The hole cutter for ostomy adhesive wafers as defined in claim 12 wherein each of said plurality of slots are aligned spiraling outwardly from said pilot on said cylindrical body bottom flat circular face, each of said plurality of slots at a different fixed distance from said cylindrical axis of said pilot.

14. The hole cutter for ostomy adhesive wafers as defined in claim 13 wherein said cutting blade defines a flat thin sheet having a protruding cutting point, said flat thin sheet also having a outwardly protruding tang, said tang adapted to engage said plurality of slots formed in said cylindrical body.

15. The hole cutter for ostomy adhesive wafers as defined in claim 14 wherein each of said plurality of slots defines a slot having trapezoidal shaped sides formed in said cylindrical body and said cutting blade defines a thin sheet with trapezoidal shaped sides, said protruding tang protruding from said thin sheet adapted to engage one of said trapezoidal shaped sides of said slot.

* * * * *